US012693211B2

(12) United States Patent
Gilead Baibich et al.

(10) Patent No.: US 12,693,211 B2
(45) Date of Patent: Jul. 28, 2026

(54) NON-CONTACT MONITORING OF FLUID CHARACTERISTICS IN WASTEWATER TRANSPORT SYSTEMS

(71) Applicant: Kando Environmental Services LTD, Tsur Yigal (IL)

(72) Inventors: Ricardo Gilead Baibich, DN Menashe (IL); Eitan Meirom, DN Lakish (IL)

(73) Assignee: Kando Environmental Services LTD, Tsur Yigal (IL)

( * ) Notice: Subject to any disclaimer, the term of this patent is extended or adjusted under 35 U.S.C. 154(b) by 0 days.

(21) Appl. No.: 17/701,291

(22) Filed: Mar. 22, 2022

(65) Prior Publication Data
US 2022/0299428 A1 Sep. 22, 2022

Related U.S. Application Data

(60) Provisional application No. 63/164,151, filed on Mar. 22, 2021.

(51) Int. Cl.
G01N 21/25 (2006.01)
G01N 21/31 (2006.01)
(Continued)

(52) U.S. Cl.
CPC ......... G01N 21/255 (2013.01); G01N 21/314 (2013.01); G01N 33/1806 (2013.01); G01N 33/1826 (2013.01); G01N 2021/6439 (2013.01)

(58) Field of Classification Search
CPC ......... G01N 21/255; G01N 2021/6439; G01N 33/1826; G01N 33/1806; G01N 21/314
See application file for complete search history.

(56) References Cited

U.S. PATENT DOCUMENTS

| | | | |
|---|---|---|---|
| 5,441,054 A | 8/1995 | Tsuchiya | |
| 2004/0171137 A1* | 9/2004 | Powers | ............. G01N 21/6486 |
| | | | 435/283.1 |
| 2018/0164217 A1* | 6/2018 | Zavaleta | ............. A61B 5/0084 |

FOREIGN PATENT DOCUMENTS

| | | | | |
|---|---|---|---|---|
| EP | 1241464 A1 * | 9/2002 | ............. | G01N 33/18 |
| WO | WO-0155717 A1 * | 8/2001 | ............. | G01N 21/64 |
| WO | WO-2020075163 A1 * | 4/2020 | ............. | C12Q 1/04 |

OTHER PUBLICATIONS

Nakamura, Kentaro, ed. Ultrasonic transducers: Materials and design for sensors, actuators and medical applications. Elsevier, 2012. (Year: 2012).*

(Continued)

*Primary Examiner* — Michelle M Iacoletti
*Assistant Examiner* — Mohamed Doumbia
(74) *Attorney, Agent, or Firm* — M&B IP Analysts, LLC

(57) ABSTRACT

A processor-based method of determining a characteristic of a fluid, the method comprising: obtaining spectral emission signature (SES) data of the fluid, wherein the SES data comprises, for one or more SES channels: intensity of radiation emitted by the fluid, in one or more channel emission frequency bands, at least partially in response to excitation of molecules of the fluid by received radiation of a respective channel transmitted frequency; and utilizing a machine learning model to determine, from the obtained SES data, data indicative of one or more characteristics of the fluid, wherein the machine learning model was trained in accordance with, at least, a plurality of training examples, one or more of the training examples comprising: SES data of a fluid sample, and one or more fluid characteristics of the fluid sample.

21 Claims, 6 Drawing Sheets

(51) Int. Cl.
_G01N 33/18_     (2006.01)
_G01N 21/64_     (2006.01)

(56)          References Cited

OTHER PUBLICATIONS

Nakamura, K. ed., 2012. Ultrasonic transducers: Materials and design for sensors, actuators and medical applications. Elsevier.) (Year: 2012).*

Anonymous: "Fluorescence spectroscopy", Wikipedia, Feb. 13, 2021 (Feb. 13, 2021), pp. 1-6.

* cited by examiner

Receive, from the fluorometer, data indicative of SES of the fluid
310

Receive fluid surface distance from water level sensor
320

Normalize the SES data in accordance with fluid surface distance
330

Provide the fluid surface distance, normalized SES data, and non-normalized SES data to fluid assessment system
340

Obtain a training set including training samples, where each training sample includes: SES data of a fluid sample, and fluid characteristics of the fluid sample
410

Train the Machine Learning Model in accordance with the training set
420

Receive, from the remote fluid sensor, data indicative of SES of the fluid
510

Using the trained Machine Learning Model, determine one or more characteristics of the fluid from the SES data
520

NON-CONTACT MONITORING OF FLUID CHARACTERISTICS IN WASTEWATER TRANSPORT SYSTEMS

TECHNICAL FIELD

The presently disclosed subject matter relates to determining fluid characteristics, and in particular to monitoring of fluid characteristics in wastewater transport systems.

BACKGROUND

Problems of monitoring characteristics of fluids in wastewater transport systems have been recognized in the conventional art and various techniques have been developed to provide solutions.

GENERAL DESCRIPTION

According to one aspect of the presently disclosed subject matter there is provided a method of determining a characteristic of a fluid, the method comprising:

a) obtaining, by a processing circuitry, at least, spectral emission signature (SES) data of the fluid, wherein the SES data comprises, for one or more SES channels:

data indicative of an intensity of radiation emitted by the fluid, in one or more channel emission frequency bands, at least partially in response to excitation of molecules of the fluid by received radiation of a respective channel transmitted frequency; and b) utilizing, by the processing circuitry, a machine learning model to determine, from the obtained SES data, data indicative of one or more characteristics of the fluid, wherein the machine learning model was trained in accordance with, at least, a plurality of training examples, one or more of the training examples comprising:

i) SES data of a fluid sample, and ii) data indicative of one or more fluid characteristics of the fluid sample.

In addition to the above features, the method according to this aspect of the presently disclosed subject matter can comprise one or more of features (i) to (xi) listed below, in any desired combination or permutation which is technically possible:

(i) at least one of the one or more fluid characteristics is selected from a group consisting of.

a. chemical oxygen demand, b. 5-day biological oxygen demand (BOD5), c. total organic content level, d. content level of total suspended solids, e. mineral oils content level, f. detergents content level, g. hydrocarbons content level, h. biomass content level, and i. turbidity.

(ii) the SES data of at least one fluid sample of the one or more training examples comprises:

for at least one of the one or more SES channels:

data indicative of an intensity of radiation emitted by the fluid, in the one or more channel emission frequency bands, at least partially in response to excitation of molecules of the fluid by received radiation of the respective channel transmitted frequency.

(iii) an SES channel of the fluid SES data has a channel transmitted frequency between 270 nanometers (nm) and 290 nm, and wherein the respective one or more channel emission frequency bands comprises an emission band including a wavelength between 340 nm and 380 nm, and an emission band including a wavelength between 420 nm and 600 nm.

(iv) an SES channel of the fluid SES data has a channel transmitted frequency between 355 nm and 375 nm, and wherein the respective one or more channel emission frequency bands comprises an emission band including a wavelength between 340 nm and 380 nm, and an emission band including a wavelength between 420 nm and 600 nm.

(v) the data indicative of an intensity of radiation emitted by the fluid comprises:

one or more radiation intensity values, wherein each radiation intensity value is indicative of a measured radiation intensity of a respective channel emission frequency band of the one or more channel emission frequency bands.

(vi) the data indicative of an intensity of radiation emitted by the fluid comprises:

one or more normalized radiation intensity values, wherein each normalized radiation intensity value is indicative of a measured radiation intensity of a respective channel emission frequency band of the one or more channel emission frequency bands, normalized in accordance with a measurement of background light.

(vii) the data indicative of an intensity of radiation emitted by the fluid comprises:

one or more normalized radiation intensity values, wherein each normalized radiation intensity value is indicative of a measured radiation intensity of a respective channel emission frequency band of the one or more channel emission frequency bands, normalized in accordance with data indicative of an intensity of transmitted radiation received at the emitting fluid.

(viii) the data indicative of an intensity of transmitted radiation received at the emitting fluid comprises data indicative of a distance between a fluorometer measuring the emitted radiation, and a surface of the emitting fluid.

(ix) the obtained SES data comprises, for one or more SES channels:

data indicative of a measured quantity of radiation emitted by the fluid in each emission frequency band of the respective SES channel;

data indicative of a normalized measure of radiation emitted by the fluid in each emission frequency band of the respective SES channel; and data indicative of a distance between a fluorometer measuring the emitted radiation, and a surface of the emitting fluid.

(x) wherein the data indicative of one or more fluid characteristics of the fluid sample is a label that is derivative of, at least, one or more characteristics selected from a group consisting of:

a. chemical oxygen demand;

b. 5-day biological oxygen demand (BOD5);

c. total organic content level;

d. content level of total suspended solids;

e. mineral oils content level;

f. detergents content level;

g. hydrocarbons content level;

h. biomass content level; and i. turbidity.

(xi) the one or more characteristics of the fluid comprises the label

According to a further aspect of the presently disclosed subject matter there is provided a system of determining a characteristic of a fluid, the system comprising a processing circuitry configured to:

a) obtain, at least, spectral emission signature (SES) data of the fluid, wherein the SES data comprises, for one or more SES channels:

data indicative of an intensity of radiation emitted by the fluid, in one or more channel emission frequency bands, at least partially in response to excitation of molecules of the fluid by received radiation of a respective channel transmitted frequency; and b) utilize a machine learning model to determine, from the obtained SES data, data indicative of one or more characteristics of the fluid, wherein the machine learning model was trained in accordance with, at least, a plurality of training examples, one or more of the training examples comprising:

i) SES data of a fluid sample, and ii) data indicative of one or more fluid characteristics of the fluid sample.

This aspect of the disclosed subject matter can further optionally comprise one or more of features (i) to (xi) listed above with respect to the method, mutatis mutandis, in any desired combination or permutation which is technically possible.

According to another aspect of the presently disclosed subject matter there is provided a computer program product comprising a non-transitory computer readable storage medium retaining program instructions, which, when read by a processing circuitry, cause the processing circuitry to perform a method of determining a characteristic of a fluid, the method comprising:

a) obtaining, at least, spectral emission signature (SES) data of the fluid, wherein the SES data comprises, for one or more SES channels:

data indicative of an intensity of radiation emitted by the fluid, in one or more channel emission frequency bands, at least partially in response to excitation of molecules of the fluid by received radiation of a respective channel transmitted frequency; and b) utilizing a machine learning model to determine, from the obtained SES data, data indicative of one or more characteristics of the fluid, wherein the machine learning model was trained in accordance with, at least, a plurality of training examples, one or more of the training examples comprising:

i) SES data of a fluid sample, and ii) data indicative of one or more fluid characteristics of the fluid sample.

This aspect of the disclosed subject matter can further optionally comprise one or more of features (i) to (xi) listed above with respect to the method, mutatis mutandis, in any desired combination or permutation which is technically possible.

According to another aspect of the presently disclosed subject matter there is provided a method of monitoring characteristics of a fluid flow, the method comprising:

receiving, by a processing circuitry, from a radiation sensor sensing radiation emitted by the fluid, data indicative of an intensity of radiation emitted by a fluid, in one or more channel emission frequency bands, at least partially in response to excitation of molecules of the fluid by received radiation of a respective channel transmitted frequency;

receiving, by the processing circuitry, data indicative of a distance between the radiation sensor and a surface of the emitting fluid; and normalizing, by the processing circuitry, the received data, in accordance with the distance.

In addition to the above features, the method according to this aspect of the presently disclosed subject matter can comprise one or more of features (xii) to (xiii) listed below, in any desired combination or permutation which is technically possible:

(xii) the method additionally comprising:

providing, by the processing circuitry, the normalized data to a system of determining fluid characteristics.

(xiii) the distance is determined, by the processing circuitry, in accordance with data from a fluid-level sensor.

According to a further aspect of the presently disclosed subject matter there is provided a system of monitoring characteristics of a fluid flow, the system comprising a processing circuitry configured to:

receive, from a radiation sensor sensing radiation emitted by the fluid, data indicative of an intensity of radiation emitted by a fluid, in one or more channel emission frequency bands, at least partially in response to excitation of molecules of the fluid by received radiation of a respective channel transmitted frequency;

receive data indicative of a distance between the radiation sensor and a surface of the emitting fluid; and normalize the received data, in accordance with the distance.

This aspect of the disclosed subject matter can further optionally comprise one or more of features (xii) to (xiii) listed above with respect to the method, mutatis mutandis, in any desired combination or permutation which is technically possible.

According to another aspect of the presently disclosed subject matter there is provided a computer program product comprising a non-transitory computer readable storage medium retaining program instructions, which, when read by a processing circuitry, cause the processing circuitry to perform a method of monitoring characteristics of a fluid flow, the method comprising:

receiving from a radiation sensor sensing radiation emitted by the fluid, data indicative of an intensity of radiation emitted by a fluid, in one or more channel emission frequency bands, at least partially in response to excitation of molecules of the fluid by received radiation of a respective channel transmitted frequency;

receiving data indicative of a distance between the radiation sensor and a surface of the emitting fluid; and normalizing the received data, in accordance with the distance.

This aspect of the disclosed subject matter can further optionally comprise one or more of features (xii) to (xiii) listed above with respect to the method, mutatis mutandis, in any desired combination or permutation which is technically possible.

BRIEF DESCRIPTION OF THE DRAWINGS

In order to understand the invention and to see how it can be carried out in practice, embodiments will be described, by way of non-limiting examples, with reference to the accompanying drawings, in which.

DETAILED DESCRIPTION

Figure 1:
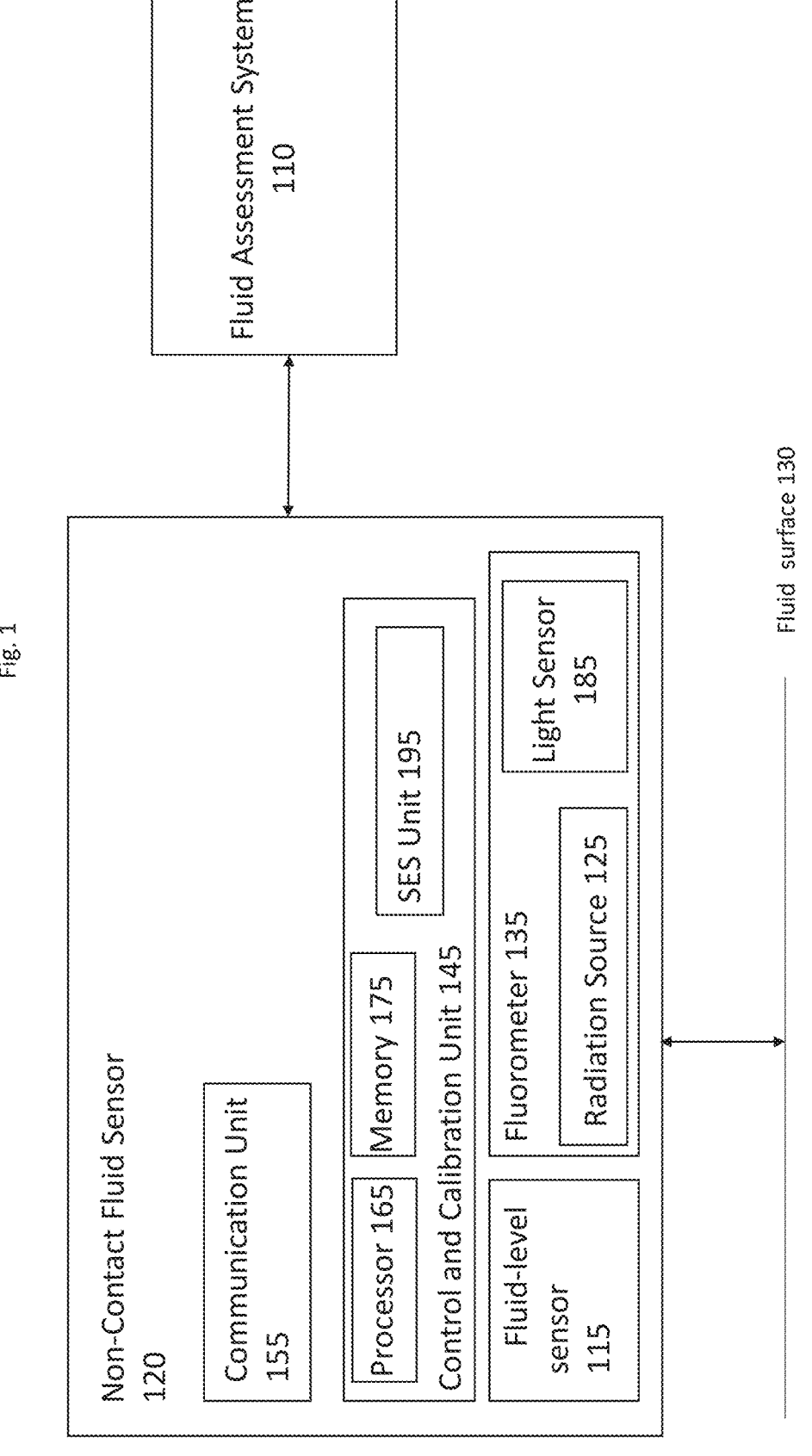
FIG. 1 illustrates an example deployment of a non-contact fluid sensor (with its components) and a fluid assessment system, in accordance with some embodiments of the presently disclosed subject matter.

In the following detailed description, numerous specific details are set forth in order to provide a thorough understanding of the invention. However, it will be understood by those skilled in the art that the presently disclosed subject matter may be practiced without these specific details. In other instances, well-known methods, procedures, components and circuits have not been described in detail so as not to obscure the presently disclosed subject matter.

Unless specifically stated otherwise, as apparent from the following discussions, it is appreciated that throughout the specification discussions utilizing terms such as "processing", "computing", "comparing", "determining", "calculating", "receiving", "providing", "obtaining", "normalizing" or the like, refer to the action(s) and/or process(es) of a computer that manipulate and/or transform data into other data, said data represented as physical, such as electronic, quantities and/or said data representing the physical objects. The term "computer" should be expansively construed to cover any kind of hardware-based electronic device with data processing capabilities including, by way of non-limiting example, the processor, mitigation unit, and inspection unit therein disclosed in the present application.

The terms "non-transitory memory" and "non-transitory storage medium" used herein should be expansively construed to cover any volatile or non-volatile computer memory suitable to the presently disclosed subject matter.

The operations in accordance with the teachings herein may be performed by a computer specially constructed for the desired purposes or by a general-purpose computer specially configured for the desired purpose by a computer program stored in a non-transitory computer-readable storage medium.

Embodiments of the presently disclosed subject matter are not described with reference to any particular programming language. It will be appreciated that a variety of programming languages may be used to implement the teachings of the presently disclosed subject matter as described herein.

In some embodiments of the presently disclosed subject matter, monitoring devices of various types of are deployed at one or more locations in a wastewater transport system. In some such embodiments, these monitoring devices communicate with one or more processor-based management/analysis systems—which can in turn be located in proximity to the monitoring devices, or can be centralized.

In some embodiments of the presently disclosed subject matter, one or more monitoring devices are immersed in wastewater flowing in the transport system, and can measure temperature, pH, salinity, electroconductivity, and/or other properties of the wastewater.

In some embodiments of the presently disclosed subject matter, one or more sampler units are placed in or near the wastewater flow, and can—for example in response to a command from a management system—capture a sample of the wastewater flow at a particular time. The captured sample can then, for example, be subject to on-site or off-site testing to determine properties of the wastewater.

Monitoring devices can transmit data indicative of the detected properties of the wastewater flow to a management/analysis system. The management/analysis system can then derive other characteristics pertaining to the wastewater. In some embodiments, these derived characteristics can in turn be utilized to assess the type of wastewater encountered by the sensor/monitor (e.g. domestic, industrial etc.) as well as to assess whether e,g, pollution events or regulatory infringements have occurred.

Fluorescence is an emission of light from a substance that has been absorbing light or other electromagnetic radiation. In some cases, the emitted light has a longer wavelength than the absorbed radiation. Phosphorescence is a related phenomenon wherein a substance is exposed to light or other radiation of a shorter wavelength, causing the substance to absorb the light and reemit it at a longer wavelength even after the radiation source is removed.

The term "fluorometer" as used herein includes devices suitable for measuring radiation emitted by a substance due to fluorescence, phosphorescence, or related phenomena.

Wastewater can include various substances including organic matter, mineral oils, detergents etc. These and other materials can include aromatic chains and other molecules which exhibit fluorescence, phosphorescence, or related radiation-emitting phenomena. Consequently, the various substances in the wastewater can emit radiation in emission frequency bands in response to molecular excitation by directed radiation. The intensities in different bands of the emitted radiation can vary in accordance with the different quantities and types of substances in the wastewater.

The measured intensity of radiation emitted by a substance at particular frequencies in response to absorbed radiation at particular applied frequencies is herein termed a spectral emission signature (SES). Spectral fluorescent signatures and spectrofluorometry in general is described—for example in: Babichenko, Sergey (ed.) "Spectral Fluorescence Signatures in Diagnostics of Water Environment" Tallinn, 2001.

In some embodiments of the presently disclosed subject matter, a machine learning model can be trained to correlate SES data to various wastewater characteristics including— by way of non-limiting example: chemical oxygen demand (COD), 5-day biological oxygen demand (BOD5), total organic content (TOC), total suspended solids (TSS), mineral oils, detergents, hydrocarbons, biomass, turbidity etc.

It is noted that the wastewater characteristics can pertain to, for example, composition of the wastewater (e.g. detergents content in parts-per-million (ppm)), behavior of the wastewater (e.g. COD), or derivative characteristics (such as whether the composition and/or behavioral characteristics of the wastewater constitute a pollution event or regulatory infringement).

In some embodiments of the presently disclosed subject matter, one or more non-contact fluid sensors are deployed at one or more locations in the wastewater transport system. The non-contact fluid sensors do not make contact with the surface of the wastewater flow, but rather monitor the flow from above it. In some embodiments, one or more non-contact fluid sensors is or includes a fluorometer—which for example directs periodic bursts of electromagnetic radiation to the surface of the wastewater flow, and measures radiation (e.g. visible light) emitted at fluorescent frequencies by organic molecules in the wastewater flow (at least partly in response to the burst)—thereby resulting in an SES of the current wastewater flow.

In some embodiments, a machine learning model can—given SES data received from, for example, a fluorometer measurement of a flow in a wastewater transport system—determine or estimate characteristics of the wastewater.

Attention is now directed to FIG. 1, which illustrates an example deployment of a non-contact fluid sensor (with its components) and a fluid assessment system, in accordance with some embodiments of the presently disclosed subject matter.

Non-contact fluid sensor 120 can be suspended above a fluid surface 130. In a case of wastewater transport system, non-contact fluid sensor 120 can be attached—for example—to a wall of a cylindrical access channel (e.g. manhole) located above the wastewater flow.

Non-contact fluid sensor 120 can include fluorometer 135. Fluorometer 135 can be a device that performs spectrofluorometry. For example: fluorometer 135 can direct electromagnetic radiation (e.g. ultraviolet light of a particular intensity) toward fluid surface 130, which then excites electrons of molecules in certain compounds and causes them to fluoresce (or phosphoresce etc.) i.e. emit radiation (for example at different frequencies from the directed radiation). Fluorometer 135 can then measure the intensities of the emitted radiation—for example at particular emission frequency bands. These measured intensities can then constitute or be comprised in an SES.

Fluorometer 135 can include radiation source 125. In some embodiments, radiation source 125 can direct a burst ultraviolet light with wavelength between 270 nm and 290 nm (for example: 280 nanometers (nm)) toward fluid surface 130. In some embodiments, radiation source 125 can direct a burst of ultraviolet light with wavelength between 355 nm and 375 nm (for example: 365 nm) toward fluid surface 130. In some embodiments, radiation source 125 can direct a burst of electromagnetic radiation of a different wavelength toward fluid surface 130. In some embodiments, radiation source 125 can direct a burst of visible light, infrared, or near-infrared radiation toward fluid surface 130.

In some embodiments, radiation source 125 is tunable—so that it can direct bursts of radiation of different configurable wavelengths.

In some embodiments, fluorometer 135 includes multiple instances of radiation source 125, where each radiation source can direct a burst of radiation of a different wavelength (for example at different times).

Fluorometer 135 can include light sensor 185. Light sensor 185 can measure light and/or other radiation emitted by the wastewater in fluid surface 130 in response to radiation originated by radiation source 125.

In some embodiments, light sensor 185 measures radiation at specific wavelengths. In some embodiments, light sensor 185 includes tunable or non-tunable filters to select particular wavelengths of interest. In some embodiments, light sensor 185 enables control of these tunable filters by—for example—control and calibration unit 145.

In some embodiments, fluorometer 135 includes multiple instances of light sensor 185, where each instance can measure radiation of a different wavelength.

In some embodiments light sensor 185 can measure radiation emitted between 340 nm and 380 nm.

In some embodiments, light sensor 185 can measure radiation emitted between 420 nm and 600 nm.

A radiation source wavelength paired with one or more light sensor wavelength ranges is herein termed a "channel". In some embodiments, fluorometer 135 enables utilization of a single channel. In some embodiments, fluorometer 135 enables utilization of multiple channels.

In some embodiments, light sensor 185 can measure background light (for example: visible light), and fluorometer 135 can provide data indicative of the intensity of the background light. The intensity of background light can be used to normalize the SES data, as described hereinbelow.

In some embodiments, fluorometer 135 enables calibration of radiation source 125 and light sensor 185. For example: in some embodiments control and calibration unit 145 can calibrate the intensity of radiation source 125 and/or the sensitivity of light sensor 185.

Non-contact fluid sensor 120 can include fluid-level sensor 115. Fluid-level sensor 115 can be any kind of suitable sensor for detecting the distance from non-contact fluid sensor 120 to fluid surface 130. For example: fluid-level sensor 115 can be an ultrasonic transducer, pulse radar sensor etc.

Fluid-level sensor 115 120 can provide the detected distance to control and calibration unit 145. Control and calibration unit 145 can then use this detected distance for control and calibration of fluorometer 135—for example: to calibrate the intensity of radiation source 125 and/or the sensitivity of light sensor 185—as will be described hereinbelow. Control and calibration unit 145 can utilize the detected distance to normalize radiation intensity data received from fluorometer 135 in accordance with the detected distance and provide the normalized radiation intensity data to fluid assessment system 110—for example via communication unit 155—as will be described hereinbelow.

Control and calibration unit 145 can additionally normalize the radiation intensity data to compensate for background light (e.g. ultraviolet light detected due to the presence of sunlight rather than the fluorescence resulting from excitation of molecules)—as will be described hereinbelow.

Control and calibration unit 145 can also provide the detected distance to fluid assessment system 110—for example via communication unit 155—as will be described hereinbelow.

Non-contact fluid sensor 120 can include communication unit 155. Communication unit 155 can be a suitable type of unit for wired and/or wireless communication between non-contact fluid sensor 120 and other entities (for example: communication unit 155 can be a unit for cellular communication)

Non-contact fluid sensor 120 can include control and calibration unit 145.

Control and calibration unit 145 can include processor 165 and memory 175. Processor 165 can be a suitable hardware-based electronic device with data processing capabilities, such as, for example, a general purpose processor, digital signal processor (DSP), a specialized Application Specific Integrated Circuit (ASIC), one or more cores in a multicore processor etc. Processor 165 can also consist, for example, of multiple processors, multiple ASICs, virtual processors, combinations thereof etc.

Memory 175 can be, for example, a suitable kind of volatile and/or non-volatile storage, and can include, for example, a single physical memory component or a plurality of physical memory components. Memory 175 can also include virtual memory. Memory 175 can be configured to, for example, store various data used in computation.

Control and calibration unit 145 can be configured to execute several functional modules in accordance with computer-readable instructions implemented on a non-transitory computer-readable storage medium. Such functional modules are referred to hereinafter as comprised in the control and calibration unit. These modules can include, for example SES unit 195.

Control and calibration unit 145 can receive data from fluid-level sensor 115, and can calibrate fluorometer 135 in accordance with the determined distance between the non-contact fluid sensor 120 and the fluid surface 130 (this distance is herein termed "fluid surface distance").

SES unit 195 can receive data from fluorometer 135 (for example: data indicative of an amount of radiation emitted by a fluid in one or more frequency bands at least partly in response to a transmitted radiation burst) can process the data, and can transmit the data (for example: to fluid assessment system 110) via communication unit 155.

Fluid assessment system 110 can be a processor-based system which receives SES data from non-contact fluid sensor 120 and determines or estimates fluid characteristics based on the SES data. Fluid assessment system 110 is described in detail below, with reference to FIG. 2. Fluid assessment system 110 can be located in within the wastewater transport channel, or can be collocated with or physically connected to non-contact fluid sensor 120. Alternatively, fluid assessment system 110 can be located remotely, and communicate with non-contact fluid sensor 120 via a cellular link or other suitable communication channel.

It is noted that the teachings of the presently disclosed subject matter are not bound by the system described with reference to FIG. 1. Equivalent and/or modified functionality can be consolidated or divided in another manner and can be implemented in any appropriate combination of software and/or hardware and executed on a suitable device. The non-contact fluid sensor (120) can be a standalone entity, or integrated, fully or partly, with fluid assessment system 110 or with other entities.

Figure 2:
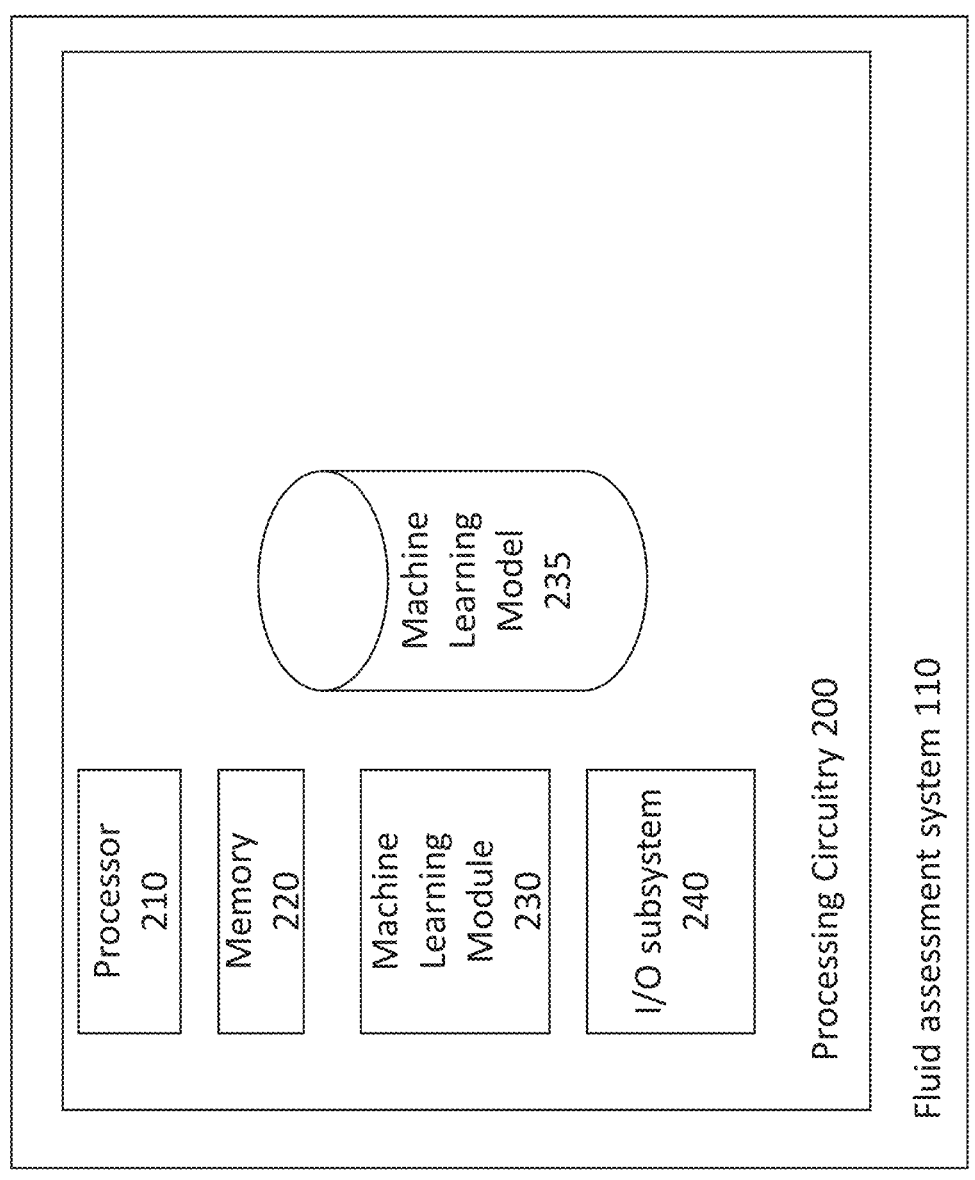
FIG. 2 illustrates a block diagram of an example of a fluid assessment system with its components, in accordance with some embodiments of the presently disclosed subject matter.

Attention is now directed to FIG. 2, which illustrates a block diagram of an example of a fluid assessment system with its components, in accordance with some embodiments of the presently disclosed subject matter.

Fluid assessment system 110 can include a processing circuitry 200. Processing circuitry 200 can include a processor 210 and a memory 220.

Processor 210 can be a suitable hardware-based electronic device with data processing capabilities, such as, for example, a general purpose processor, digital signal processor (DSP), a specialized Application Specific Integrated Circuit (ASIC), one or more cores in a multicore processor etc. Processor 210 can also consist, for example, of multiple processors, multiple ASICs, virtual processors, combinations thereof etc.

Memory 220 can be, for example, a suitable kind of volatile and/or non-volatile storage, and can include, for example, a single physical memory component or a plurality of physical memory components. Memory 220 can also include virtual memory. Memory 220 can be configured to, for example, store various data used in computation.

Processing circuitry 200 can be configured to execute several functional modules in accordance with computer-readable instructions implemented on a non-transitory computer-readable storage medium. Such functional modules are referred to hereinafter as comprised in the processing circuitry. These modules can include, for example, machine learning module 230, and Input/Output (I/O) subsystem 240.

Machine learning module 230 can implement any suitable type of machine leaning method (e.g. support vector machines, random forest etc.). Machine learning module 230 can store data in machine learning model 235, which can be any kind of suitable data storage. Machine learning model 230 can, for example, be trained to correlate SES and optional associated data to wastewater characteristics, as described hereinbelow.

I/O subsystem 240 can control interactions with other system elements. For example I/O subsystem 240 can communicate with non-contact fluid sensor 120. I/O subsystem 240 can also display assessment output data to a screen or transmit it to another entity for display or further processing.

It is noted that fluid assessment system 110 can be collocated with non-contact fluid sensor 120. In this case, SES unit 195 and other modules/functions described above with reference to FIG. 1 can be comprised in processing circuitry 200.

It is noted that the teachings of the presently disclosed subject matter are not bound by the system described with reference to FIG. 2. Equivalent and/or modified functionality can be consolidated or divided in another manner and can be implemented in any appropriate combination of software and/or hardware and executed on a suitable device. The fluid assessment system 110 can be a standalone entity, or integrated, fully or partly, with non-contact fluid sensor 120 or with other entities.

Figure 3A:
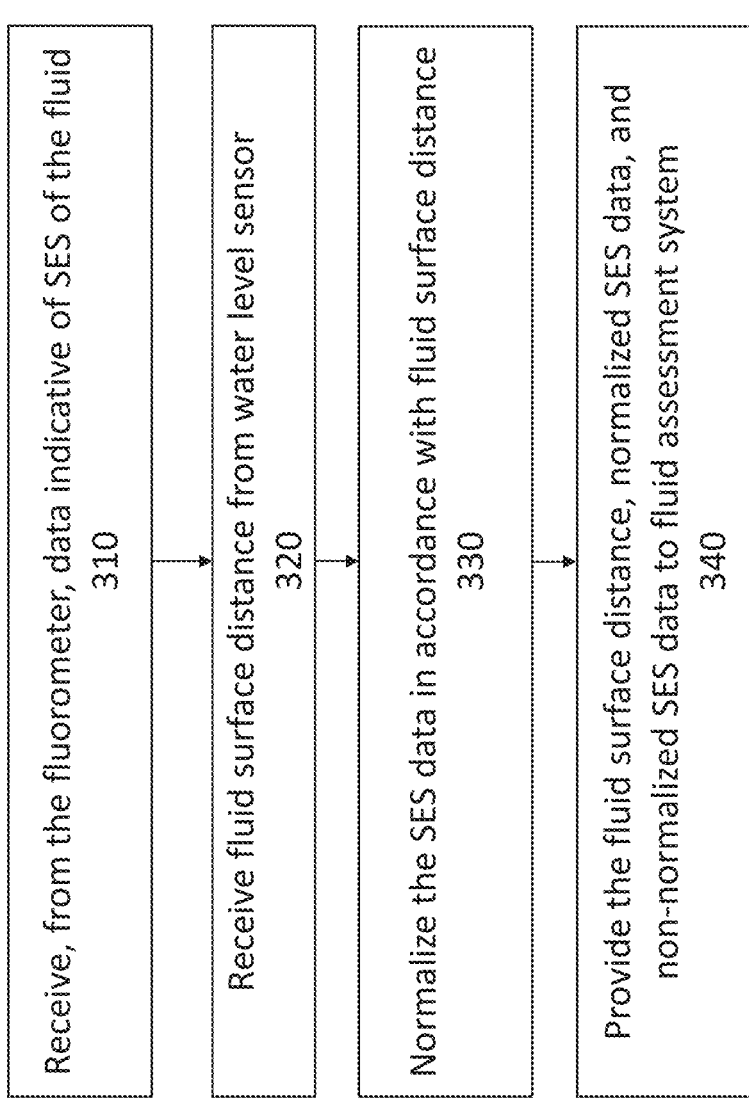
FIG. 3A illustrates a flow diagram of an example method of obtaining spectral emission signature data for determining characteristics of a fluid, in accordance with some embodiments of the presently disclosed subject matter.

Attention is now directed to FIG. 3A, which illustrates a flow diagram of an example method of obtaining spectral emission signature data for determining characteristics of a fluid, in accordance with some embodiments of the presently disclosed subject matter.

Non-contact fluid sensor 120 (for example: SES unit 195) can receive (310), from the fluorometer 135 (e.g. light sensor 285/radiation sensor), SES data of the fluid.

In some embodiments, the SES data includes a vector of unitless light intensity values, where each intensity value corresponds to a light intensity of one or more monitored emission frequency bands of a single channel—as measured by the fluorometer 135—. emitted at least partially in response to excitation of molecules of the fluid by a received radiation burst of a respective transmit wavelength.

In some embodiments, the SES data includes 2 or more such vectors—where each vector corresponds to a distinct channel and is accordingly associated with a respective transmit wavelength.

Non-contact fluid sensor 120 (for example: SES unit 195) can receive (320) data indicative of the distance between remote fluid sensor 120 and fluid surface 130 (i.e. the fluid surface distance)—for example as received from fluid-level sensor 115.

Non-contact fluid sensor 120 (for example: SES unit 195) can next normalize (330) the SES data in accordance with the fluid surface distance.

It is noted that radiation intensity can decay in accordance with distance travelled, and that the intensity of transmitted radiation arriving at fluid surface 130 can consequently diminish in accordance with the square of the distance between radiation source 125 and fluid surface 130. It is further noted that the intensity of the light emitted by the fluid can consequently vary in accordance with this distance due to the diminished excitation of molecules of the fluid.

Accordingly, in some embodiments, non-contact fluid sensor 120 (for example: SES unit 195) normalizes the SES data e.g. adjusts the vector of light intensity values in accordance with the fluid surface distance from the radiation source at the time of measurement of the sample.

In some embodiments, non-contact fluid sensor 120 (for example: SES unit 195) normalizes the SES data in accordance with detected background light e.g. non-contact fluid sensor 120 (for example: SES unit 195) can receive data indicative of a level of background visible light (for example: from light sensor 185), and can adjust the SES data to compensate for the likelihood that radiation detected in the channel emission frequency bands include background light. In some embodiments, non-contact fluid sensor 120 (for example: SES unit 195) performs normalization of data to compensate for background light in addition to performing normalization in accordance with fluid surface distance (or other data indicative of intensity of transmitted radiation received by the fluid). In some embodiments, non-contact fluid sensor 120 (for example: SES unit 195) performs only background light normalization, or only fluid surface distance compensation.

Non-contact fluid sensor 120 (for example: SES unit 195) can then provide (340) the normalized SES data to fluid assessment system 110. In some embodiments, non-contact fluid sensor 120 (for example: SES unit 195) provides the fluid surface distance and non-normalized SES together with the normalized SES data to fluid assessment system 110. Fluid assessment system 110 can then utilize this data in conjunction with its machine learning model to determine one or more fluid characteristics, as described hereinbelow.

The processing of SES data described herein with reference to FIG. 3A is a non-limiting example which enables the fluid assessment system 110 to receive SES data which has been adjusted to compensate for radiation decay resulting from fluid surface distance.

SES data can be adjusted in other ways in order to perform this compensation. By way of non-limiting example, an estimate of intensity of transmitted radiation reaching fluid surface 130 can be included together with non-normalized SES data—instead of the normalized SES data.

Figure 3B:
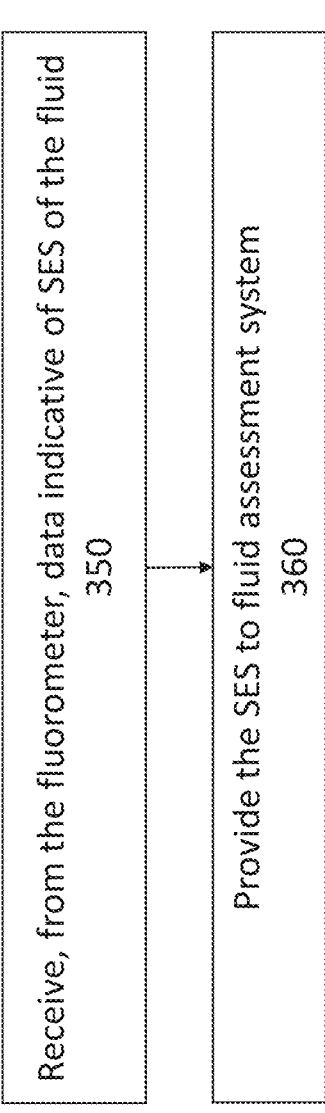
FIG. 3B illustrates a flow diagram of an alternative example method of obtaining spectral emission signature data for determining characteristics of a fluid, in accordance with some embodiments of the presently disclosed subject matter.

FIG. 3B illustrates a flow diagram of a simplified example method of obtaining spectral emission signature data for determining characteristics of a fluid, in accordance with some embodiments of the presently disclosed subject matter.

In the method of FIG. 3B, non-contact fluid sensor 120 (for example: SES unit 195) can receive (350) SES data (e.g. as described above with reference to FIG. 3A) and provide (360) it to fluid assessment system 110 without any preprocessing.

It is noted that the teachings of the presently disclosed subject matter are not bound by the flow diagrams illustrated in FIGS. 3A-3B, and that in some cases the illustrated operations may occur concurrently or out of the illustrated order (for example: operations 310 and 320). It is also noted that whilst the flow chart is described with reference to elements of the system of FIG. 1, this is by no means binding, and the operations can be performed by elements other than those described herein.

Figure 4:
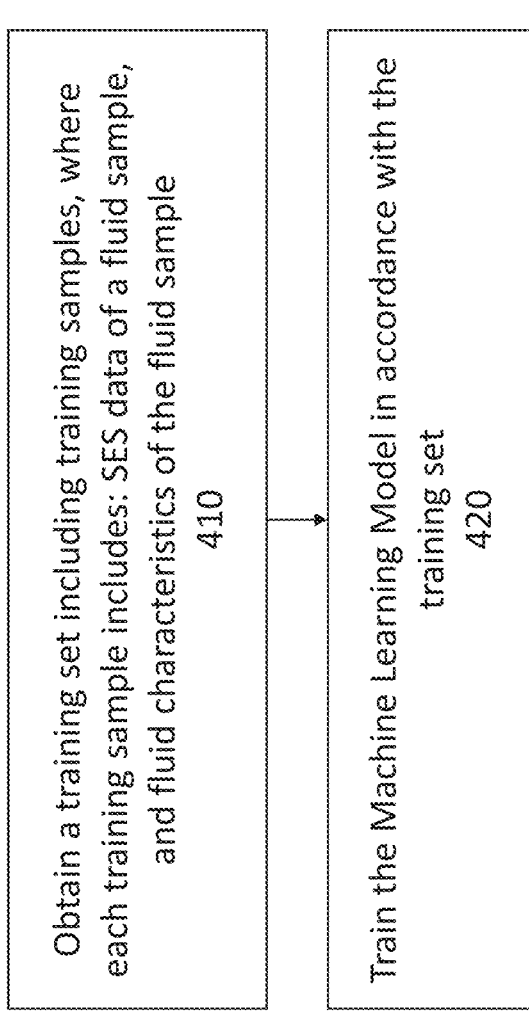
FIG. 4 illustrates a flow diagram of an example method of training a machine learning model to derive fluid characteristics from spectral emission signature (SES) data, in accordance with some embodiments of the presently disclosed subject matter.

Attention is now directed to FIG. 4, which illustrates a flow diagram of an example method of training a machine learning model to derive fluid characteristics from spectral emission signature (SES) data, in accordance with some embodiments of the presently disclosed subject matter.

Processing circuitry 200 (for example: machine learning module 230) can obtain (410) a training set including training samples, wherein at least one training sample (for example: each training sample) includes, at least:

SES data of a fluid sample, and data indicative of one or more ground truth fluid characteristics of the fluid sample.

In some embodiments, the SES data includes data indicative of an intensity of radiation emitted by the fluid in each of one or more emission frequency bands, responsive to excitation of molecules of the fluid by an intensity of received radiation of a particular transmitted frequency. That is to say that the SES data can include data on intensity of emissions of a single channel.

In some embodiments, the transmitted wavelength of a channel is between 270 nm and 290 nm (for example: 280 nm).

In some embodiments, the transmitted wavelength of a channel is between 355 nm and 375 nm (for example: 365 nm), In some embodiments, one emission frequency band of a channel is between 420 nm and 600 nm.

In some embodiments, one emission frequency band of a channel is between 340 nm and 380 nm.

In some embodiments, the SES data includes a vector of unitless light intensity values, where each intensity value corresponds to a light intensity of one emission frequency band of a single channel.

In some embodiments, the SES data includes data indicative of intensities of radiation emitted by the fluid in each of one or more emission frequency bands, responsive to excitation of molecules of the fluid by received burst radiation of respective transmitted frequencies. That is to say that the SES data can include data on intensity of emissions of multiple channels. In such embodiments, the SES data can include 2 or more vectors of unitless light intensity values, where the data in each vector corresponds to a distinct channel.

In some embodiments, the SES data of the sample additionally includes data indicative of the intensity of transmitted radiation received at the fluid (for a particular channel) in a particular sample. By way of non-limiting example: SES data can include fluid surface distance which indicates intensity of transmitted radiation received at the fluid for a particular transmission intensity.

In some embodiments, the SES data of the sample includes compensation for variation in the intensity of transmitted radiation received at the fluid in different samples. By way of non-limiting example: the intensity data can be normalized, as described above with reference to FIG. 3A.

In some embodiments, the SES data of the sample includes:

fluid surface distance normalized intensity data, and non-normalized intensity data.

In some embodiments, the SES data pertaining to one or more of the training samples is obtained by monitoring of actual wastewater in a wastewater transport system by a non-contact fluid sensor 120, and ground truth fluid characteristics of the sample derive from contact monitoring of the wastewater flow and/or laboratory analysis of captured wastewater flow.

In some embodiments, the SES data pertaining to one or more of the training samples is obtained from a simulation or approximation of non-contact fluid sensor behavior.

In some embodiments, the SES data pertaining to one or more of the training samples is obtained from a different suitable source.

The ground truth fluid characteristics of the training sample can include, for example, characteristics that are at least partially derived from one or more of:

a) COD b) BOD5 c) TOC level d) TSS content level e) mineral oils content level f) detergents content level g) hydrocarbons content level h) biomass content level i) turbidity By way of non-limiting example: the ground truth fluid characteristics of the training sample can include one or more of a)-i).

By way of non-limiting example: ground truth fluid characteristics of the training sample can include a derivative characteristic e.e. "pollution event" fluid characteristic that is derivative of other characteristics (such one or more of as fluid characteristics a)-i) above and/or other fluid characteristics).

Processing circuitry 200 (for example: machine learning module 230) can then train (420) machine learning model 235 in accordance with the training set, for example by using machine learning training methods as known in the art. By way of non-limiting example: processing circuitry 200 (for example: machine learning module 230) can perform feature extraction on a training sample, and use extracted features to train machine learning model 235.

It is noted that the teachings of the presently disclosed subject matter are not bound by the flow diagrams illustrated in FIG. 4, and that in some cases the illustrated operations may occur concurrently or out of the illustrated order (for example: operations 410 and 420). It is also noted that whilst the flow chart is described with reference to elements of the system of FIGS. 1-2, this is by no means binding, and the operations can be performed by elements other than those described herein.

Figure 5:
FIG. 5 illustrates a flow diagram of an example method of utilizing a machine learning model to determine characteristics of a fluid from spectral emission signature data, in accordance with some embodiments of the presently disclosed subject matter.

Attention is now directed to FIG. 5, which illustrates a flow diagram of an example method of utilizing a machine learning model to determine characteristics of a fluid from spectral emission signature data, in accordance with some embodiments of the presently disclosed subject matter.

Processing circuitry (200) (e.g. machine learning module 230) can receive (510), from the non-contact fluid sensor 120, SES data of a fluid (e.g. a fluid at fluid surface 130 at a particular time as detected by fluorometer 135).

In some embodiments, the received SES data includes data indicative of an intensity of radiation emitted by the fluid in each of one or more emission frequency bands, responsive to excitation of molecules of the fluid by an intensity of received radiation of a particular transmitted frequency. That is to say that the SES data can include data on intensity of emissions of a single channel.

In some embodiments, the transmitted wavelength of a channel is between 270 nm and 290 nm (for example: 280 nm).

In some embodiments, the transmitted wavelength of a channel is between 355 nm and 375 nm (for example: 365 nm), In some embodiments, one emission frequency band of a channel is between 420 nm and 600 nm.

In some embodiments, one emission frequency band of a channel is between 340 nm and 380 nm.

In some embodiments, the received SES data includes data indicative of intensities of radiation emitted by the fluid in each of one or more groups of emission frequency bands, responsive to excitation of molecules of the fluid by respective intensities of received radiation of a respective transmitted frequencies. That is to say that the received SES data can include data on intensity of emissions of multiple channels.

In some embodiments, the received SES data includes one or more vectors of unitless light intensity values, where each intensity value in the vector corresponds to a light intensity of one emission frequency band of the channel.

In some embodiments, the transmitted frequency of a first channel of the multiple channels is between 270 nm and 290 nm (for example: 280 nm), one emission frequency band of the first channel is between 420 nm and 600 nm, and another emission frequency band of the first channel is between 340 nm and 380 nm. In some such embodiments, the transmitted frequency of a second channel of the multiple channels is between 355 nm and 375 nm (for example: 365 nm), one emission frequency band of the second channel is between 420 nm and 600 nm, and another emission frequency band of the second channel is between 340 nm and 380 nm.

In some embodiments, the received SES data additionally includes data indicative of the intensity of transmitted radiation received at the fluid (for a particular channel). By way of non-limiting example: SES data can include fluid surface distance which indicates intensity of transmitted radiation received at the fluid for a particular transmission intensity.

In some embodiments, the received SES data has been adjusted for variation in the intensity of transmitted radiation received at the fluid in different measurement instances. By way of non-limiting example: the intensity data can be normalized, as described above with reference to FIG. 3A.

In some embodiments, the received SES data includes:

data indicative of a measured intensity of radiation emitted by the fluid data indicative of a normalized measure of intensity of radiation emitted by the fluid, and data indicative of a distance between a fluorometer measuring the emitted radiation, and a surface of the emitting fluid.

In some embodiments, the received SES data includes the same specific data as the samples that were used to train machine learning model 235 as described above with reference to FIG. 4.

Processing circuitry (200) (e.g. machine learning module 230) can utilize (520) machine learning model 235 to determine or one or more characteristics of the fluid—for example by using suitable machine learning classification methods as known in the art.

In some embodiments, the utilizing machine learning model 235 to determine or one or more characteristics of the fluid includes feature extraction.

In some embodiments, the determined fluid characteristics of the fluid sample include, for example one or more fluid characteristics that are at least partially derived from one or more of:

a) COD b) BOD5 c) TOC level d) TSS content level e) mineral oils content level f) detergents content level g) hydrocarbons content level h) biomass content level i) turbidity By way of non-limiting example: the determined fluid characteristics of the training sample can include one or more of a)-i).

By way of non-limiting example, the determined fluid characteristics of the training sample can include a derivative characteristic e.g. a "pollution event" fluid characteristic that is derivative of other characteristics (such as one or more fluid characteristics a)-i) above and/or other fluid characteristics).

It is noted that the teachings of the presently disclosed subject matter are not bound by the flow diagrams illustrated in FIG. 5. It is also noted that whilst the flow chart is described with reference to elements of the system of FIGS. 1-2, this is by no means binding, and the operations can be performed by elements other than those described herein.

It is to be understood that the invention is not limited in its application to the details set forth in the description contained herein or illustrated in the drawings. The invention is capable of other embodiments and of being practiced and carried out in various ways. Hence, it is to be understood that the phraseology and terminology employed herein are for the purpose of description and should not be regarded as limiting. As such, those skilled in the art will appreciate that the conception upon which this disclosure is based may readily be utilized as a basis for designing other structures, methods, and systems for carrying out the several purposes of the presently disclosed subject matter.

It will also be understood that the system according to the invention may be, at least partly, implemented on a suitably programmed computer. Likewise, the invention contemplates a computer program being readable by a computer for executing the method of the invention. The invention further contemplates a non-transitory computer-readable memory tangibly embodying a program of instructions executable by the computer for executing the method of the invention.

Those skilled in the art will readily appreciate that various modifications and changes can be applied to the embodiments of the invention as hereinbefore described without departing from its scope, defined in and by the appended claims.

The invention claimed is:

1. A method of determining a characteristic of a fluid in a wastewater transport channel, the method comprising;

determining, by a fluid-level sensor and a first processing circuitry (PC), a distance between a radiation source and a surface of a fluid in the wastewater transport channel;

tuning a filter, on the radiation source, to a unique wavelength;

directing, by the first PC, a radiation from the radiation source, in one or more spectral emission signature (SES) channels, toward the fluid in the transport channel, wherein each of the one or more SES channels has a channel transmitted frequency, and wherein the channel transmitted frequency has the unique wavelength;

obtaining, by a second processing circuitry, at least, SES data of the fluid, wherein the SES data comprises, for the one or more SES channels:

data indicative of an intensity of radiation emitted by the fluid, in one or more channel emission frequency bands, wherein the radiation emitting by the fluid is emitted at least partially in response to an excitation of molecules of the fluid by the directed radiation from the radiation source at a respective channel transmitted frequency; and utilizing, by the second processing circuitry, a machine learning model to determine, from the obtained SES data, data indicative of one or more characteristics of the fluid, wherein the machine learning model was trained in accordance with, at least, a plurality of training examples, wherein the plurality of training examples includes:

SES data of a fluid sample, and data indicative of the one or more characteristics of the fluid sample.

2. The method of claim 1, wherein at least one of the one or more determined characteristics of the fluid is selected from the group consisting of:

chemical oxygen demand;

5-day biological oxygen demand (BOD5);

total organic content level content level of total suspended solids;

mineral oils content level;

detergents content level;

hydrocarbons content level;

biomass content level; and turbidity.

3. The method of claim 1, wherein the SES data of a fluid sample of the plurality of training examples comprises:

for one or more SES channels:

data indicative of an intensity of radiation emitted by the fluid sample, in a respective channel emission frequency band, at least partially in response to an excitation of molecules of the fluid sample by a radiation of a respective channel transmitted frequency that is directed toward the fluid sample.

4. The method of claim 1, wherein:

an SES channel of the one or more SES channels has a channel transmitted frequency between 270 nanometers (nm) and 290 nm, and respective channel emission frequency bands that are at least one of: a wavelength between 340 nm and 380 nm and a wavelength between 420 nm and 600 nm.

5. The method of claim 1, wherein:

an SES channel of the one or more SES channels has a channel transmitted frequency between 355 nm and 375 nm, and a respective channel emission frequency bands that are at least one of: a wavelength between 340 nm and 380 nm and a wavelength between 420 nm and 600 nm.

6. The method of claim 1, wherein the data indicative of an intensity of radiation emitted by the fluid comprises:

one or more radiation intensity values, wherein each radiation intensity value is indicative of a measured radiation intensity of a respective channel emission frequency band of the one or more channel emission frequency bands.

7. The method of claim 1, wherein the data indicative of an intensity of radiation emitted by the fluid comprises:

one or more normalized radiation intensity values, wherein each normalized radiation intensity value is indicative of a measured radiation intensity of a respective channel emission frequency band of the one or more channel emission frequency bands that are normalized in accordance with a measurement of a background light.

8. The method of claim 1, wherein the data indicative of an intensity of radiation emitted by the fluid comprises:

one or more normalized radiation intensity values, wherein each normalized radiation intensity value is indicative of a measured radiation intensity of a respective channel emission frequency band of the one or more channel emission frequency bands that are normalized in accordance with data indicative of an intensity of transmitted radiation received at the emitting fluid.

9. The method of claim 8, wherein the data indicative of an intensity of transmitted radiation received at the emitting fluid comprises data indicative of a distance between a fluorometer measuring the radiation emitted by the fluid and a surface of the emitting fluid.

10. The method of claim 1, wherein the obtained SES data comprises, for one or more SES channels:

data indicative of a measured quantity of the radiation emitted by the fluid in each channel emission frequency band of the respective SES channel;

data indicative of a normalized measure of the radiation emitted by the fluid in each channel emission frequency band of the respective SES channel; and data indicative of a distance between a fluorometer measuring the emitted radiation emitted by the fluid and a surface of the emitting fluid.

11. The method of claim 2, wherein the data indicative of one or more fluid characteristics of the fluid sample is a label that is a derivative of at least one of the one or more characteristics.

12. A system of determining a characteristic of a fluid in a wastewater transport channel, the system comprising:

a first processing circuitry, the first processing circuitry being configured to:

determine, by a fluid-level sensor and a first processing circuitry (PC), a distance between a radiation source and a surface of a fluid in the wastewater transport channel;

tune a filter, on the radiation source, to a unique wavelength;

direct, by the first PC, a radiation from the radiation source, in one or more spectral emission signature (SES) channels, toward the fluid in the transport channel, wherein each of the one or more SES channels has a channel transmitted frequency, and wherein the channel transmitted frequency has the unique wavelength;

a second processing circuitry, the second processing circuitry being configured to:

obtain, at least spectral emission signature (SES) data of the fluid, wherein the SES data comprises, for the one or more SES channels:

data indicative of an intensity of radiation emitted by the fluid, in one or more channel emission frequency bands, wherein the radiation emitting by the fluid is emitted at least partially in response to an excitation of molecules of the fluid by a the directed radiation from the radiation source at a respective channel transmitted frequency; and utilize a machine learning model to determine, from the obtained SES data, data indicative of one or more characteristics of the fluid, wherein the machine learning model was trained in accordance with, at least, a plurality of training examples, wherein the plurality of the training examples includes:

SES data of a fluid sample, and data indicative of the one or more characteristics of the fluid sample.

13. A computer program product comprising:

a first non-transitory computer readable storage medium retaining program instructions, which, when read by a processing circuitry, cause the processing circuitry to perform a computerized method of determining a characteristic of a fluid in a wastewater transport channel, the method comprising:

determining, by a fluid-level sensor and a first processing circuitry (PC), a distance between a radiation source and a surface of a fluid in the wastewater transport channel, tuning a filter, on the radiation source, to a unique wavelength; and directing, by the first PC, radiation, from the radiation source, in one or more spectral emission signature (SES) channels, toward the fluid in the transport channel, wherein each of the one or more SES channels has a channel transmitted frequency, and wherein the channel transmitted frequency has the unique wavelength;

a second non-transitory computer readable storage medium retaining program instructions, which, when read by a processing circuitry, cause the processing circuitry to perform a computerized method of determining a characteristic of a fluid, the method comprising:

obtaining, at least spectral emission signature (SES) data of the fluid, wherein the SES data comprises, for the one or more SES channels:

data indicative of an intensity of radiation emitted by the fluid, in one or more channel emission frequency bands, wherein the radiation emitting by the fluid is emitted at least partially in response to excitation of molecules of the fluid by the directed radiation from the radiation source at a respective channel transmitted frequency, and utilizing a machine learning model to determine, from the obtained SES data, data indicative of one or more characteristics of the fluid, wherein the machine learning model was trained in accordance with, at least, a plurality of training examples, wherein the plurality of training examples includes:

SES data of a fluid sample, and data indicative of the one or more characteristics of the fluid sample.

14. A system of monitoring characteristics of a fluid flow in a wastewater transport channel, the system comprising:

a processing circuitry, the processing circuitry comprising a processor and a memory, wherein the processing circuitry is configured to:

tune a filter, on a radiation sensor, to a unique wavelength;

emit a radiation burst, via the radiation source, at a channel transmitted frequency toward the fluid flow, wherein the channel transmitted frequency has the unique wavelength;

measure, from an operably connected radiation sensor, a sensing radiation emitted by the fluid flow, wherein an intensity of the sensing radiation emitted by the fluid, in one or more channel emission frequency bands, at least partially in response to excitation of molecules of the fluid by the emitted radiation burst of the channel transmitted frequency;

detect a distance between the radiation sensor and a surface of the fluid flow via an operably connected ultrasonic transducer, wherein the operably connected ultrasonic transducer provides data indicative of the distance between the radiation sensor and the surface of the fluid flow; and normalize the data measured by the sensor, in accordance with the detected distance.

15. The system of claim 14, the processing circuitry being additionally configured to:

provide the normalized data to a system of determining fluid characteristics.

16. A method of monitoring characteristics of a fluid flow in a wastewater transport channel, the method comprising:

tuning a filter, on a radiation sensor, to a unique wavelength;

emitting a radiation burst, via a radiation source, of a channel transmitted frequency toward the fluid flow, wherein the channel transmitted frequency has a unique wavelength;

measuring, by a processing circuitry, from an operably connected radiation sensor, a sensing radiation emitted by the fluid flow, wherein an intensity of the sensing radiation emitted by the fluid, in one or more channel emission frequency bands, at least partially in response to excitation of molecules of the fluid by the emitted radiation burst of the channel transmitted frequency;

detecting, by the processing circuitry, from an operably connected ultrasonic transducer that is configured to provide data indicative of a distance between the radiation sensor and the surface of the fluid flow; and normalizing the data measured by the radiation, in accordance with the detected distance.

17. A computer program product comprising a non-transitory computer readable storage medium retaining program instructions, which, when read by a processing circuitry, cause the processing circuitry to perform a computerized method of monitoring characteristics of a fluid flow in a wastewater transport channel, the method comprising:

tuning a filter, on a radiation sensor, to a unique wavelength;

emitting a radiation burst, via a radiation source, of a channel transmitted frequency toward the fluid flow, wherein the channel transmitted frequency has a unique wavelength;

measuring, from an operably connected radiation sensor, a sensing radiation emitted by the fluid flow, wherein an intensity of the sensing radiation emitted by the fluid, in one or more channel emission frequency bands, at least partially in response to excitation of molecules of the fluid by the emitted radiation burst of the channel transmitted frequency;

detecting, from an operably connected ultrasonic transducer that is configured to provide data indicative of a distance between the radiation sensor and the surface of the fluid flow; and normalizing the data measured by the radiation, in accordance with the detected distance.

18. The method of claim 1, wherein the first processing circuitry is the second processing circuitry.

19. The method of claim 1, further comprising:

causing a display via a device connected to the fluid assessment system on the determined one or more fluid characteristics.

20. The system of claim 14, wherein the processing circuitry is further configured to:

tune a filter, on the light sensor, to measure emission by fluid flow at one or more channel emission frequency bands, wherein each of the one or more channel emission frequency bands has unique wavelengths.

21. The system of claim 14, wherein the channel transmitted frequency is a unique wavelength selected from at least one spectral emission signature (SES) channel, wherein the each of the at least one SES channel has a pair of a channel transmitted frequency and one or more channel emission frequency bands.

* * * * *